(12) United States Patent
Guezuraga et al.

(10) Patent No.: US 9,566,127 B1
(45) Date of Patent: Feb. 14, 2017

(54) STAIRWAY APPARATUS FOR USE WITH ENDOSCOPE CABINETS

(71) Applicants: Aubrey Guezuraga, Lenexa, KS (US); David Guezuraga, Kansas City, MO (US); Barry Gilman, Platte City, MO (US)

(72) Inventors: Aubrey Guezuraga, Lenexa, KS (US); David Guezuraga, Kansas City, MO (US); Barry Gilman, Platte City, MO (US)

( * ) Notice: Subject to any disclaimer, the term of this patent is extended or adjusted under 35 U.S.C. 154(b) by 0 days.

(21) Appl. No.: 15/156,190

(22) Filed: May 16, 2016

Related U.S. Application Data

(60) Provisional application No. 62/161,458, filed on May 14, 2015.

(51) Int. Cl.
*E04F 11/02* (2006.01)

(52) U.S. Cl.
CPC ............ *A61B 50/10* (2016.02); *E04F 11/02* (2013.01); *A47B 2220/05* (2013.01); *A61B 2050/105* (2016.02); *E04F 2011/0203* (2013.01)

(58) Field of Classification Search
CPC ...... A47B 2220/05; E06C 1/005; E04F 11/05; E04F 2011/0203; A47C 12/00
USPC .................. 312/235.1; 52/182, 184; 182/206
See application file for complete search history.

(56) References Cited

U.S. PATENT DOCUMENTS

| | | | | |
|---|---|---|---|---|
| 361,983 A * | 4/1887 | Brown | .................... | G02B 27/34 250/462.1 |
| 4,599,835 A * | 7/1986 | Rinke | .................... | E04H 4/144 52/169.7 |
| 4,846,304 A * | 7/1989 | Rasmussen | ............ | A47B 77/10 182/129 |
| D322,872 S * | 12/1991 | Holbrook | .................... | 119/28.5 |
| 5,085,290 A * | 2/1992 | Guirlinger | .............. | E06C 1/005 182/77 |
| 5,131,492 A * | 7/1992 | Caminiti | .............. | A47B 46/005 182/156 |
| 7,815,266 B2 * | 10/2010 | Sun | .......................... | G06F 1/18 312/223.1 |
| 2009/0188754 A1 * | 7/2009 | Warren | .................... | E06C 1/397 182/141 |
| 2010/0191049 A1 * | 7/2010 | Mandava | ........... | A61B 19/0248 600/102 |
| 2014/0097954 A1 * | 4/2014 | Mandava | ........... | A61B 19/0248 340/539.1 |

(Continued)

FOREIGN PATENT DOCUMENTS

NL  EP 0709049 A1 *  5/1996  ............. A47B 97/00

*Primary Examiner* — Robert Canfield
(74) *Attorney, Agent, or Firm* — Plager Schack LLP

(57) ABSTRACT

A stairway apparatus for use with an endoscope storage cabinet includes a slidable door to open or close the cabinet's interior compartment. The stairway apparatus includes a base member disposed on a ground and placed against the cabinet, the base member having a first step with a front face, a rear face opposite the front face, and a top face connecting the front and rear faces, the front face having a lip coupled thereto and positioned to remain flush with the top face of the first step. The front face of the first step contacts front edges of the cabinet. The lip extends into the interior compartment of the cabinet when open and contacts side walls of the cabinet, thereby preventing lateral movement of the base member.

7 Claims, 4 Drawing Sheets

(56) References Cited

U.S. PATENT DOCUMENTS

| | | | |
|---|---|---|---|
| 2015/0001005 A1* | 1/2015 | Goodson | A47B 77/00 182/96 |
| 2015/0090528 A1* | 4/2015 | Binegar | A47C 12/00 182/12 |
| 2016/0222673 A1* | 8/2016 | Brink | E04F 11/025 |

* cited by examiner

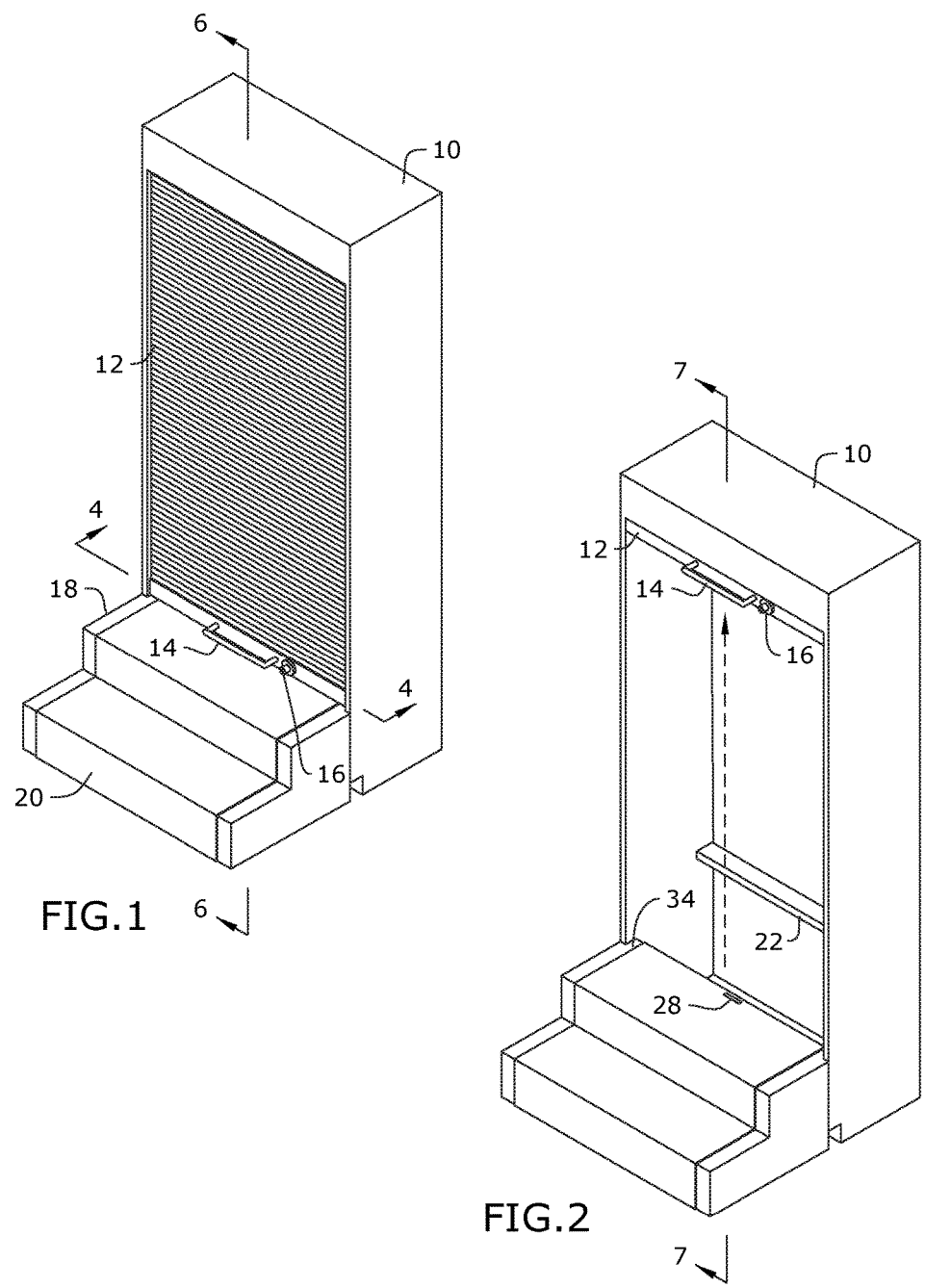

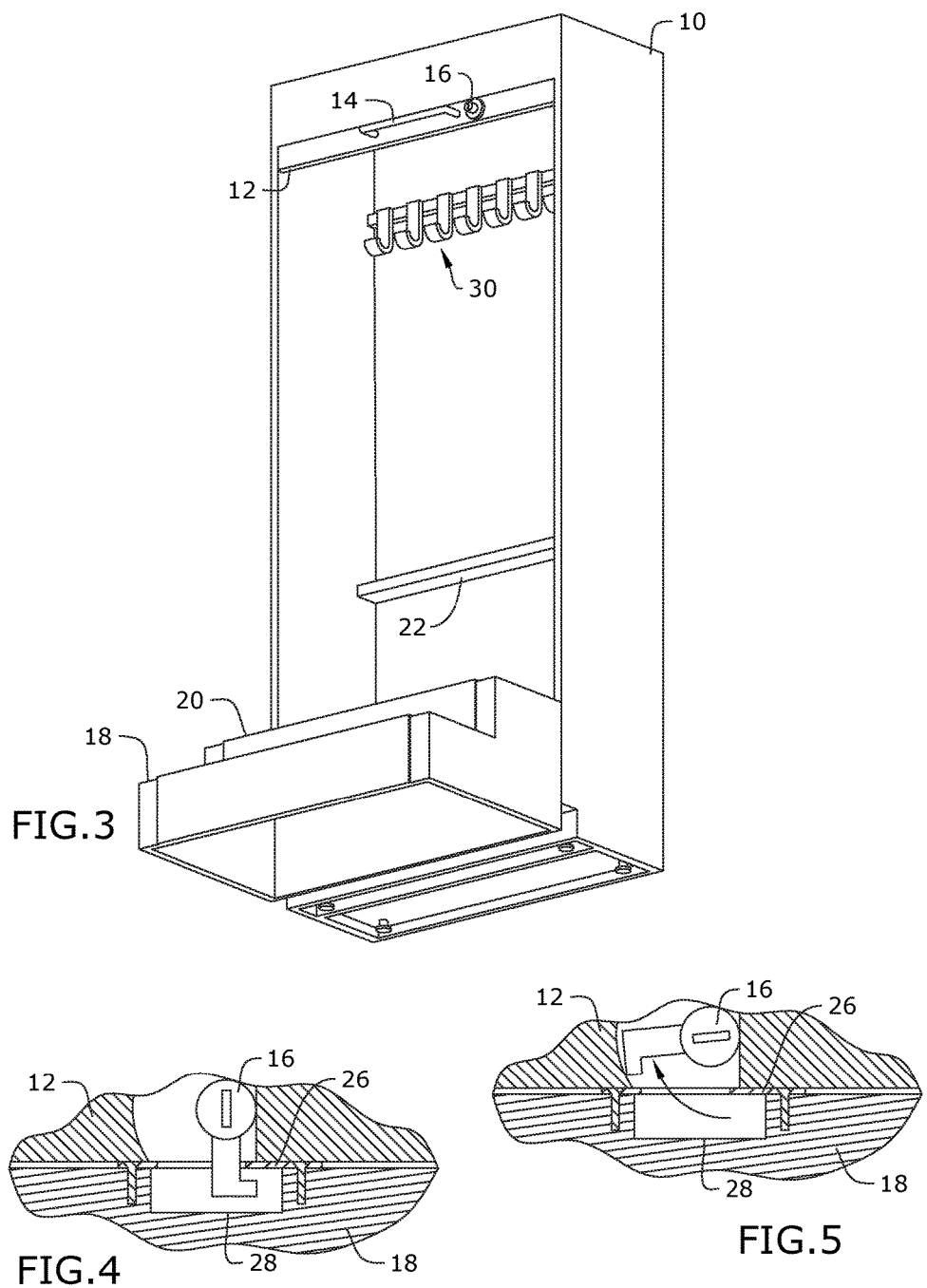

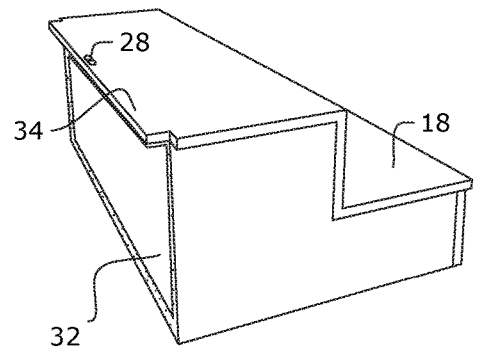
FIG.8
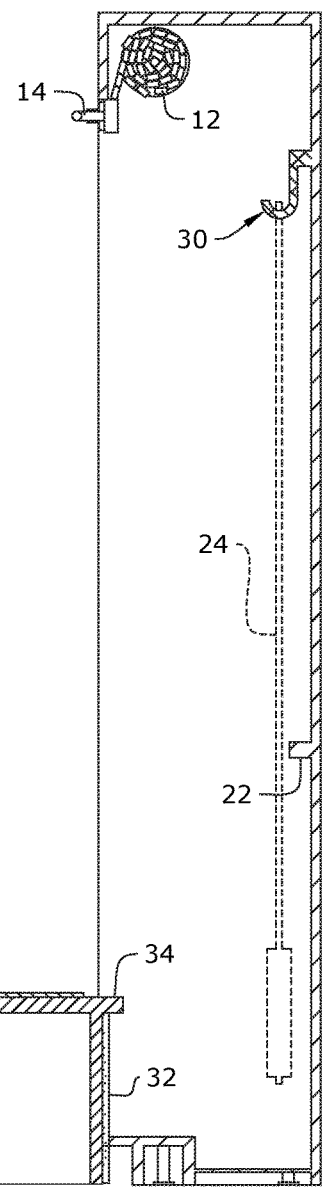
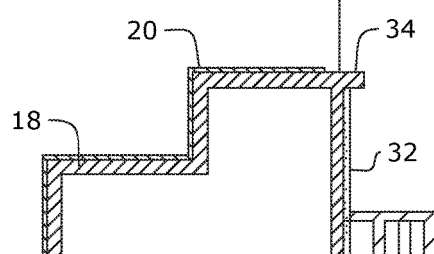
FIG.7

STAIRWAY APPARATUS FOR USE WITH ENDOSCOPE CABINETS

RELATED APPLICATION

The application claims priority to provisional patent application U.S. Ser. No. 62/161,458 filed on May 14, 2015, the entire contents of which is herein incorporated by reference.

BACKGROUND

The embodiments herein relate generally to cabinets for storing medical equipment.

Medical equipment such as endoscopes are generally stored in cabinets when not in use. In order to prevent a contamination of the equipment, special safety and handling measures are taken by users to prevent each endoscope from coiling, touching another endoscope or unsanitary surface when hung inside of the cabinet. This protects the endoscope from contamination and enhances the lifetime of the equipment.

Since endoscopes are hung upright within the cabinet, it is not uncommon for the cabinet to have a height of at least 100 inches. This height makes it difficult for users to maneuver the endoscopes within the cabinet, which increases the chance of mishandling the equipment. Users sometimes place stools within the cabinets to help increase their reach height. However, the stool in this configuration promotes the transfer of germs and/or bacteria to the cabinet and creates a tripping hazard.

Several step devices for cabinets exist as disclosed in U.S. Pat. No. 7,815,266 and U.S. Patent Application Publication 2015/0001005. However, these step devices are undesirable because a significant portion of each device is inserted within the cabinet. This reduces cabinet storage space and is problematic in cabinets used for storing medical equipment. In particular, the insertion of a significant portion of the device within the cabinet increases the likelihood the device and/or user contacts the stored medical equipment. This greatly increases the risk of contaminating the medical equipment.

As such, there is a need in the industry for a stairway apparatus for use with endoscope storing cabinets that addresses the limitations of the prior art, which improves the user's ability to maneuver any endoscopes within the cabinet while reducing the likelihood of contamination to the medical equipment.

SUMMARY

A stairway apparatus for use with a cabinet that stores a plurality of endoscopes is provided. The cabinet comprises a slidable door to open or close an interior compartment of the cabinet. The stairway apparatus is configured to aid a user in maneuvering the endoscopes within the cabinet while reducing a contamination risk by minimizing inadvertent contact between each endoscope and another object. The stairway apparatus comprises a base member disposed on a ground and placed against the cabinet, the base member comprising a first step, the first step comprising a front face, a rear face opposite the front face, and a top face connecting the front and rear faces, the front face comprising a lip coupled thereto and positioned to remain flush with the top face of the first step, wherein the front face of the first step is configured to contact front edges of the cabinet, wherein the lip is configured to extend into the interior compartment of the cabinet when open and contact side walls of the cabinet, thereby preventing lateral movement of the base member.

BRIEF DESCRIPTION OF THE FIGURES

The detailed description of some embodiments of the invention will be made below with reference to the accompanying figures, wherein the figures disclose one or more embodiments of the present invention.

FIG. 1 depicts a perspective view of certain embodiments of the stairway apparatus with a cabinet shown in a closed position;

FIG. 2 depicts a perspective view of certain embodiments of the stairway apparatus with the cabinet shown in the open position and strike plate 26 removed for illustrative clarity;

FIG. 3 depicts a bottom perspective view of certain embodiments of the stairway apparatus with the cabinet shown in the open position;

FIG. 4 depicts a section view of certain embodiments of the stairway apparatus taken along line 4-4 in FIG. 1 with the cabinet in the locked position;

FIG. 5 depicts a section view of certain embodiments of the stairway apparatus with the cabinet in the unlocked position;

FIG. 7 depicts a section view of certain embodiments of the stairway apparatus taken along line 7-7 in FIG. 2; and FIG. 8 depicts a perspective view of certain embodiments of the stairway apparatus with strike plate 26 and stair covering 20 removed for illustrative clarity.

DETAILED DESCRIPTION OF CERTAIN EMBODIMENTS

Figure 6:
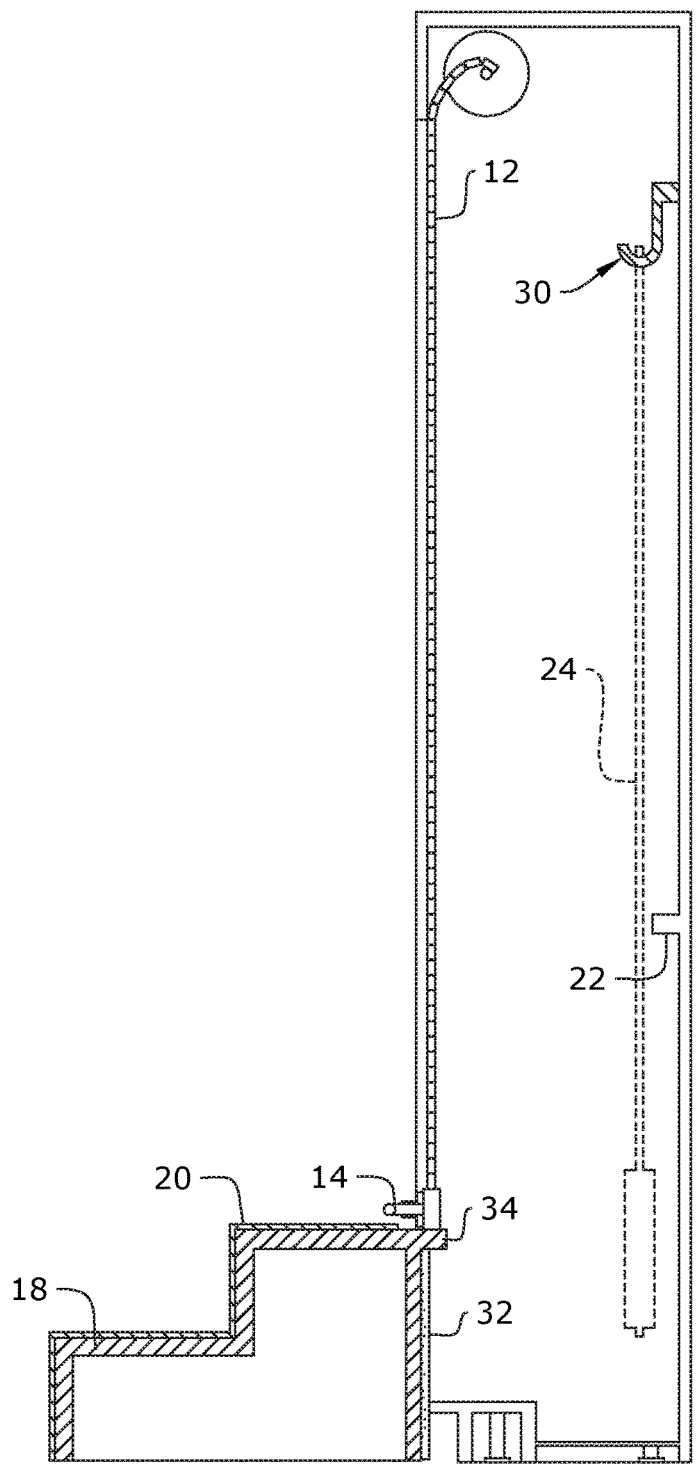
FIG. 6 depicts a section view of certain embodiments of the stairway apparatus taken along line 6-6 in FIG. 1.

As depicted in FIGS. 1-3, stairway apparatus 18 is configured for use with cabinet 10, which is configured to store a plurality of endoscopes (not shown). Cabinet 10 generally comprises slidable door 12, handle 14, and latch 16. Slidable door 12 preferably is a tambour door that can slidably adjust to a closed position as shown in FIG. 1 or an open position as shown in FIG. 2. Once slidable door 12 is in the open position, the interior compartment of cabinet 10 is exposed, which comprises hooks 30 and separator shelf 22. Each hook 30 is configured to secure an endoscope (not shown). In certain embodiments, separator shelf 22 may comprises slots (not shown) to receive the stored endoscopes and prevent them from contacting each other.

Stairway apparatus 18 generally comprises a plurality of steps and may be made from various materials known in the field including, but not limited to, wood, stainless steel, other metals, or the like. In one embodiment, stairway apparatus 18 comprises an upper step and a lower step. However, it shall be appreciated that stairway apparatus 18 may comprise any alternative number of steps to accommodate different sized cabinets.

In certain embodiments, stair covering 20 is coupled to the upper and lower steps of stairway apparatus 18 to enhance grip when a user (not shown) is positioned on either step. Stair covering 20 is preferably made from plastic, but may include other materials such as fabric, rubber, other materials, and the like. In an alternative embodiment, a plurality of wheels (not shown) may be secured to the bottom of stairway apparatus 18 to permit a user to easily transport the apparatus from one location to another.

As depicted in FIG. 8, foam pad 32 is coupled to the front face of stairway apparatus 18 by an adhesive. However, alternative fastening components may be used instead. Foam pad 32 is a compressible and resilient member that prevents endoscopes stored within cabinet 10 from becoming damaged upon contact with foam pad 32.

The upper step of stairway apparatus 18 comprises lip 34, which extends out from the front face of stairway apparatus 18. In a preferred embodiment, lip 34 is coupled to a central portion of the top edge of the front face of stairway apparatus 18. Lip 34 remains flush with the top face of the upper step of stairway apparatus 18.

In operation, stairway apparatus 18 is disposed on the ground and positioned against the front side of cabinet 10 as shown in FIGS. 1-2 and 6. In this position, the front face of stairway apparatus 18 contacts front edges of cabinet 10. Lip 34 extends into the interior compartment of cabinet 10 and contacts side walls of the cabinet. This contact between lip 34 and the side walls of cabinet 10 prevents lateral movement of stairway apparatus 18. Ultimately, this enhances the stability of stairway apparatus 18 when in use. The user (not shown) can climb onto stairway apparatus 10 to maneuver any endoscopes 24 within cabinet 10.

Since the majority of stairway apparatus 18 resides outside of cabinet 10 with the exception of lip 34, space within the interior compartment of cabinet 10 is not significantly reduced. The likelihood that any endoscope 24 contacts stairway apparatus 18 is greatly reduced, which minimizes the chance the medical equipment becomes contaminated.

In the closed position depicted in FIGS. 1 and 6, slidable door 12 of cabinet 10 rests on lip 34. In the open position depicted in FIGS. 2 and 7, the interior compartment of cabinet 10 is exposed. In certain embodiments of the invention, slidable door 12 is configured to lock with stairway apparatus 18. In particular, lip 34 of stairway apparatus 18 comprises opening 28. In a preferred embodiment, strike plate 26 is coupled to opening 28 as depicted in FIGS. 4-5. Latch 16 of slidable door 12 is configured to communicate with opening 28 when disposed on lip 34. Latch 16 is preferably a rotatable hook member that may be adjusted by a tool such as a key. As depicted in FIG. 4, latch 16 may be adjusted to rotate the hook member to engage with strike plate 26 in the locked position. In this locked position, the hook member of latch 16 prevents slidable door 12 from opening. As depicted in FIG. 5, latch 16 may be adjusted to rotate the hook member to disengage with strike plate 26 to the unlocked position. In the unlocked position, slidable door 12 is free to open.

It shall be appreciated that the components of stairway apparatus 18 described in several embodiments herein may comprise any alternative known materials in the field and be of any color, size and/or dimensions. It shall be appreciated that the components of stairway apparatus 18 described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A stairway apparatus for use with a cabinet that stores a plurality of endoscopes, the cabinet comprising a slidable door to open or close an interior compartment of the cabinet, the stairway apparatus configured to aid a user in maneuvering the endoscopes within the cabinet while reducing a contamination risk by minimizing inadvertent contact between each endoscope and another object, the stairway apparatus comprising:
a base member disposed on a ground and placed against the cabinet, the base member comprising a first step, the first step comprising a front face, a rear face opposite the front face, and a top face connecting the front and rear faces, the front face comprising a lip coupled thereto and positioned to remain flush with the top face of the first step, wherein the front face of the first step is configured to contact front edges of the cabinet, wherein the lip is configured to extend into the interior compartment of the cabinet when open and contact side walls of the cabinet, thereby preventing lateral movement of the base member.

2. The stairway apparatus of claim 1, wherein the lip is coupled to a central portion of a top edge of the front face of the first step.

3. The stairway apparatus of claim 2, further comprising a second step coupled to the rear face of the first step, wherein the first step comprises a first height and the second step comprises a second height, wherein the second height is less than the first height.

4. The stairway apparatus of claim 3, further comprising a foam pad coupled to the front face of the first step.

5. The stairway apparatus of claim 4, wherein the slidable door is configured to rest on the lip of the first step when closed.

6. The stairway apparatus of claim 5, wherein the lip of the first step comprises an opening and a strike plate coupled thereto, wherein a latch of the slidable door is configured to engage with the strike plate to lock the slidable door to the stairway apparatus.

7. The stairway apparatus of claim 6, further comprising a cover coupled to the first and second steps.

* * * * *